United States Patent [19]

Curtin

[11] Patent Number: 4,823,476
[45] Date of Patent: Apr. 25, 1989

[54] METHOD AND APPARATUS FOR MEASURING PHYSICAL ATTRIBUTES OF A HUMAN BODY

[76] Inventor: Marilyn A. Curtin, 2245 Woodside La., #7, Sacramento, Calif. 95825

[21] Appl. No.: 120,337

[22] Filed: Nov. 13, 1987

Related U.S. Application Data

[63] Continuation of Ser. No. 895,765, Aug. 12, 1986, abandoned, which is a continuation-in-part of Ser. No. 698,650, Feb. 6, 1985, abandoned.

[51] Int. Cl.$^4$ ............................ G01B 3/02; A41H 1/02
[52] U.S. Cl. ..................................... 33/512; 33/1 K; 33/1 R; 33/277
[58] Field of Search ................. 33/512, 513, 515, 514, 33/2 R, 511, 277, 1 R, 1 K

[56] References Cited

U.S. PATENT DOCUMENTS

| | | | |
|---|---|---|---|
| 865,418 | 9/1907 | Moe | 33/2 R |
| 1,414,481 | 5/1922 | Moe | 33/2 R |
| 1,415,833 | 5/1922 | Ginsburg | 33/277 |
| 2,619,729 | 12/1952 | Jarnette | 33/515 |
| 2,752,689 | 7/1956 | Adams et al. | 33/513 |
| 2,780,004 | 2/1957 | Rosenbaum | 33/512 |
| 3,340,784 | 9/1967 | Zimberoff | 33/1 R |

FOREIGN PATENT DOCUMENTS 470356 12/1950 Canada ................................. 33/494

Primary Examiner—William D. Martin, Jr.
Attorney, Agent, or Firm—Skjerven, Morrill, MacPherson, Franklin & Friel

[57] ABSTRACT

Method and apparatus are provided to measure a plurality of physical attributes of a human body in relation to the values of these attributes in a theoretically ideal human body. In one embodiment, by means of a novel proportional panel and measurement guide, a wide range of human body heights can be accommodated in a single measuring structure.

9 Claims, 6 Drawing Sheets

METHOD AND APPARATUS FOR MEASURING PHYSICAL ATTRIBUTES OF A HUMAN BODY

CROSS-REFERENCE TO RELATED APPLICATION

This application is a continuation of copending application Ser. No. 895,765, filed Aug. 12, 1986, which in turn was a continuation-in-part of copending application Ser. No. 698,650, filed Feb. 6, 1985, both now abandoned.

BACKGROUND OF THE INVENTION

1. Field of the Invention

This invention relates in general to methods and apparatus for measuring selected attributes of a human body, and relates more particularly to measuring such attributes in relation to the values of these attributes in a theoretically ideal human body.

2. Prior Art

Leonardo DaVinci developed a scientific scale of measurement employing a comprehensive set of proportions for drawing the human figure. He did extensive research on the human body and bone structure, and used this research in much of his art work. According to principles used by Leonardo, the height of the head becomes a "yardstick" to measure the rest of the body. In this concept of an ideal body, the entire body height as eight times the height of the head. DaVinci's principles using head height in relation to the rest of the body are:

1. Starting from the feet, the distance to the base of the calf is one head.
2. The distance from the base of the calf to the bottom of the knee is the next head.
3. To mid-thigh is three heads.
4. To the top of the thigh is four heads and the mid-point of the body.
5. The fifth part is from mid-point (top of thigh) to the waist.
6. The sixth part is from waist to the underarm.
7. The seventh part is from underarm to the chin.
8. The head itself is the eighth section.

For understanding the entire human body structure, it is important to divide the body into these small sections, seeing each individually, in order to put the body back together in a way that makes sense.

SUMMARY OF THE INVENTION

The present invention expands on DaVinci's principles to develop methods and apparatus for measuring a plurality of attributes of a human body in relation to the values of these attributes for a theoretically ideal human body of the same height as the body being measured. The invention involves the use of a proportional panel having divisions thereon adjacent to which a human body to be measured is positioned. The panel includes a plurality of spaced sloping lines, the lines on one edge of the panel being graduated over a distance representing the minimum height of a human body to be measured, and the lines on the other edge of the panel being graduated over a distance representing the maximum height of a body to be measured.

The panel member is laterally movable so that it can be positioned adjacent a body to be measured and adjacent a vertical measurement guide. With a person standing behind the transparent measurement guide on the centerline thereof, the moveable panel member is positioned so that the top sloping line thereon passes through the measurement guide centerline at the top of the measured person's head. A suitable horizontal marker or indicator is then applied to the measurement guide at the height at which the top sloping line passes through the centerline, this height corresponding to the height of the person being measured.

Then, a plurality of additional horizontal markers are placed on the measurement guide at each of the positions at which the other sloping lines cross the measurement guide centerline. The total number of such markers applied to the measurement guide is at least eight, corresponding to DaVinci's eight divisions of the ideal human body as discussed above. By placing the measured person behind the transparent measurement guide, the location of the markers on the guide indicates the ideal eight divisions of a human body of that persons height, and variations in the measured person's body divisions from the ideal divisions are readily apparent by reference to a measuring scale on the measurement guide.

Another aspect of the present invention involves the use of transparent members having grids thereon which would be positioned adjacent to a human face, or an image thereof, to measure variations in characteristics of the human head from the ideal head.

DESCRIPTION OF THE PREFERRED EMBODIMENT

Figure 1:
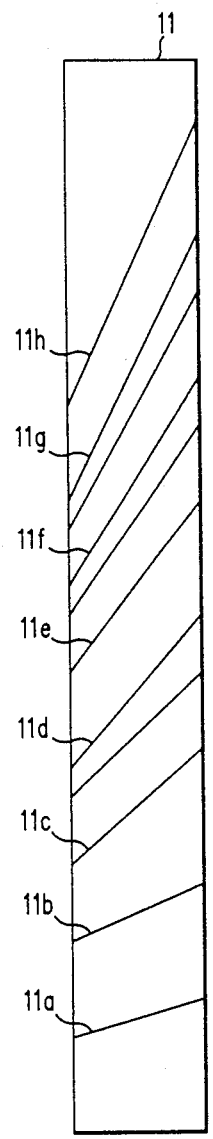
FIG. 1 illustrates the proportional panel of the present invention.

FIG. 1 illustrates one embodiment of a proportional panel usable in the present invention. Panel 11 is made of a rigid transparent material, such as clear plastic. Panel 11 is provided with a plurality of sloping lines extending across the panel face, the lines sloping upwardly from left to right in the illustrated embodiment. In FIG. 1, 8 such sloping lines, 11a–11h, are shown, the ends of the lines at the right edge of panel 11 being equally spaced from each other as are the ends of the lines at the left edge of the panel. These sloping lines provide a proportional device to accommodate persons of different height. For example, if the minimum body height to be measured is 4 feet, 8 inches (56 inches), the left hand edges of the 8 lines 11a–11h would be spaced apart by 7 inches. Similarly, if the maximum height to be accommodated is 6 feet, 8 inches (80 inches), the right hand edges of lines 11a–11h would be spaced 10 inches from each other. However, these representative distances can be varied to accommodate larger or smaller ranges of human height without departing from the spirit of the invention.

Figure 2:
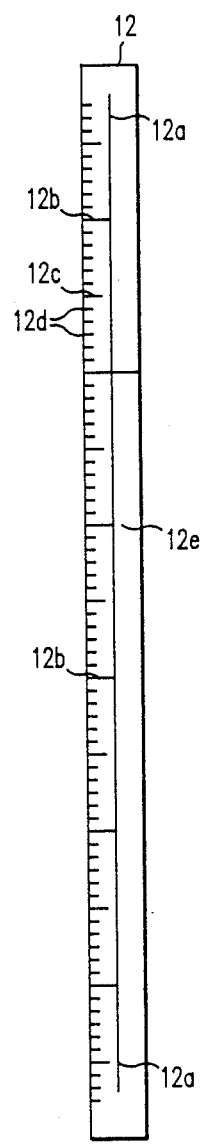
FIG. 2 illustrates one embodiment of a measurement guide for use with the panel of FIG. 1.

One embodiment of a measurement guide is shown in FIG. 2. Guide 12 is made of a rigid transparent material and is calibrated with a vertical centerline mark 12a extending essentially the length of the guide. Guide 12 also is provided with a plurality of horizontal reference marks. Such marks may include lines 12b spaced at one foot intervals along guide 12, shorter lines 12c spaced at the half foot intervals between lines 12b, and still shorter lines or marks 12d at one inch intervals. Guide 12 is also provided with a strip 12e of pressure sensitive adhesive or fabric extending on the right side of guide 12 for a substantial portion of its length. Adhesive strip 12e is utilized to temporarily secure the markers to the guide, as will be described in more detail below.

Figure 3:
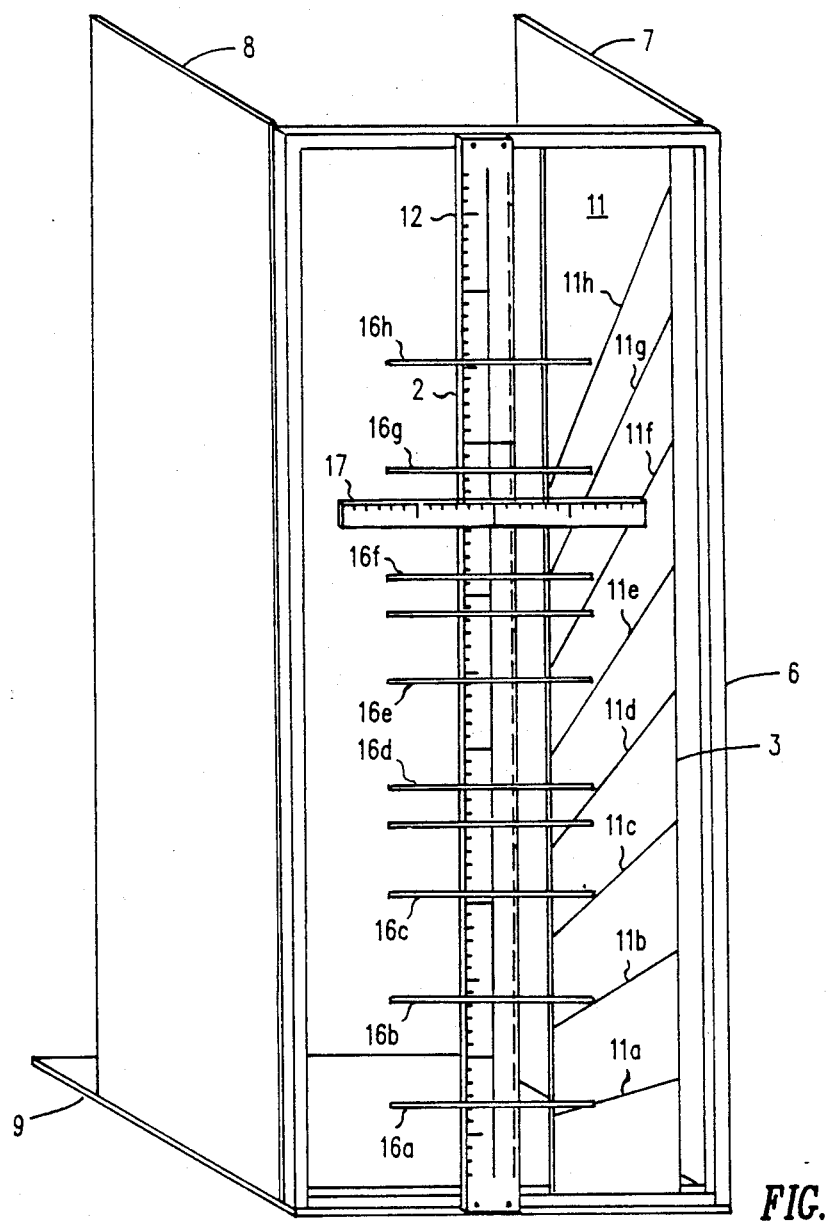
FIG. 3 is a perspective view of structure for carrying out the present invention.

The perspective view of FIG. 3 illustrates structure for utilizing the proportional panel 11 and the measurement guide 12 in practicing the present invention. Such structure includes a housing having side panels 7 and 8, a bottom or floor portion 9, and an open front section defined by a frame member 6. Side panels 7 and 8 and bottom portion 9 are also preferably made of rigid transparent material, and if desired these members may be hinged to frame member 6 so that the side and bottom members may be folded when the structure is not in use or is to be transported.

Measurement guide member 12 is rigidly secured to the top and bottom portions of frame 6 in approximately the center thereof. Proportional panel 11 is mounted for lateral movement on frame 6, and such movement may be made possible by providing rollers on the top end of panel 11, the rollers riding on a track or path in the top portion of frame 6. The lower end of panel 11 is guided in a track or channel in the bottom of frame 6. Panel 11 is disposed to slide laterally within frame 6 and pass behind member 12.

Figure 4:
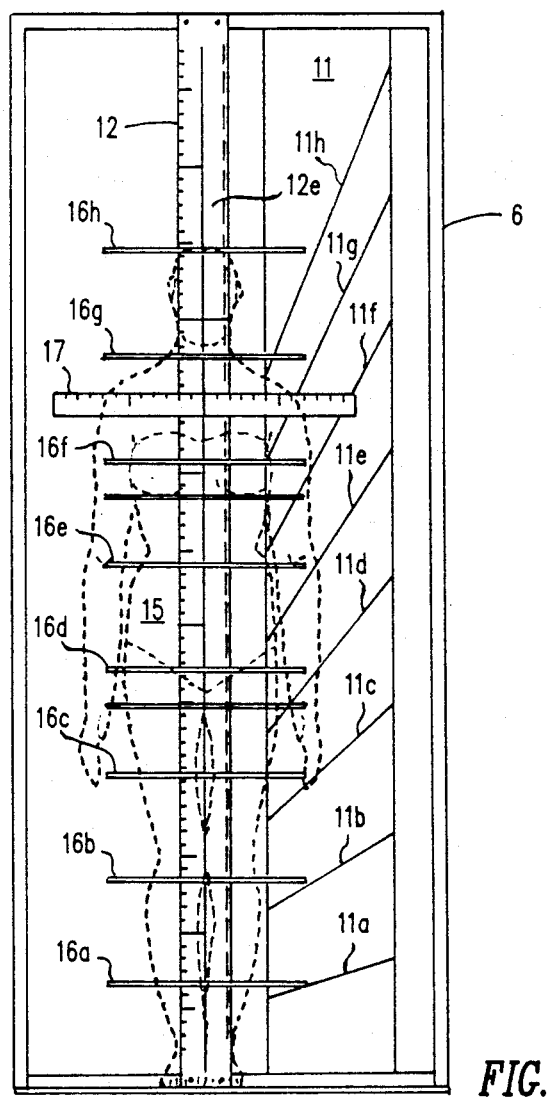
FIGS. 4 and 5 are frontal and side views, respectively, illustrating the use of this invention.

The use and practice of the present invention is illustrated in FIG. 4 where a person 15 is placed behind guide 12, and panel 11 is moved laterally to the left until the top sloping line 11h crosses centerline 12a at the top of the measured person's head. A marker or rod 16h is then placed on guide 12 corresponding to the level of the top of the measured person's head. Rod 16 may be provided with a pressure sensitive adhesive or fabric similar to that on guide 12 to insure adherence of the rod to guide 12 for the period of use and to facilitate removal of rod 16 after such use.

Next, other rods 16a–16g are placed on guide 12 at those levels where the remaining sloping lines 11a–11g cross centerline 12a of guide 12. The locations of these rods on guide 12 then represent the division lines for the eight divisions of the ideal human body for a person of that height.

Information relative to differences between the ideal body and the measured body is readily apparent by comparing the locations of rods 16a–16h with the scale on the left side of guide 12 and determining the differences. Such information may be obtained in any suitable manner, such as by having an operator record such differences, by photographing the person and measuring the differences from the resulting photograph or by employing sensors to provide information for processing in a computer.

The invention has particular application to dress and hair styling in advising persons of particular styles or fashions which would be most flattering to their particular body configuration. For example, hemlines are usually adjusted relative to the knee location. The second rod from the bottom of FIG. 4, rod 16b, represents the location of the knee on an ideal body for that particular height, and a recommendation can be made to choose a hemline which results in the "appearance" of a knee located at the ideal level. Similarly, in FIG. 4, the fifth rod, 16e, indicates the center of an ideal body, where the legs connect to the torso. This should be ½ the total body length. Again, appropriate clothing adjustments can be made to give the impression of that ideal proportion where it is lacking in fact.

If desired, sloping lines in addition to the eight ideal body division lines 11a–11h may be utilized on panel 11 as an indication of the location of the mid-thigh or the end of the torso for comparison with the location of the fingertips or wrist, respectively. Additionally, a member 17 having a measuring scale thereon may be employed on guide 12 as a measure of shoulder level to aid in selecting lapels.

Figure 5:
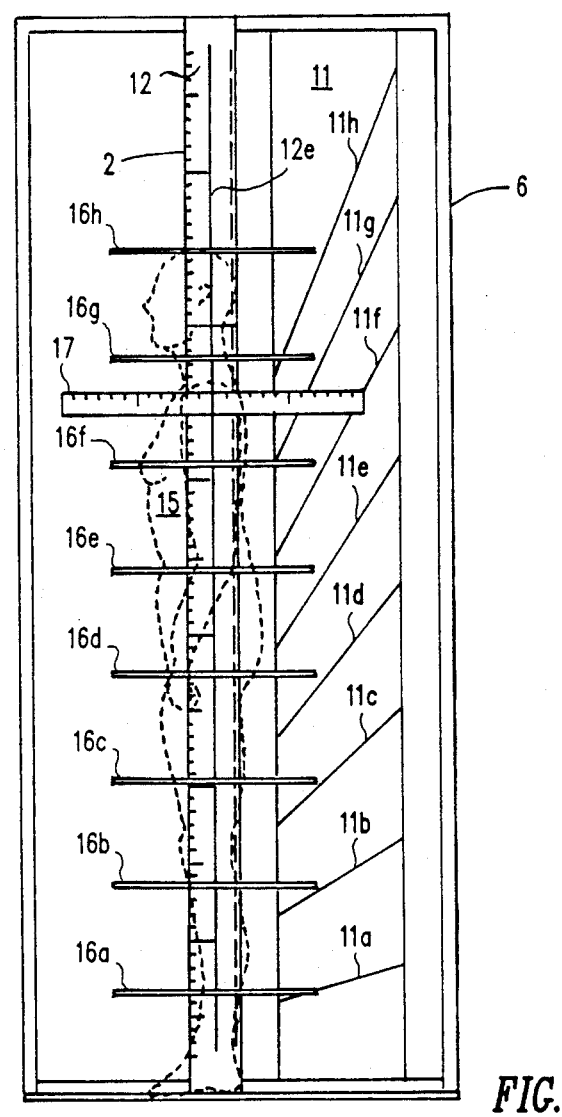

Similarly, as best seen in FIG. 5, a side view of a person can be useful in selecting hairstyles based on the head shape relative to a centerline passing through the head just in front of the ear. The application of the invention as shown in FIG. 5 is a valuable tool in determining the degree of body lean and head placement.

Although described above in connection with dress, the invention is also useful in other areas such as medicine and chiropractic.

Figure 6:
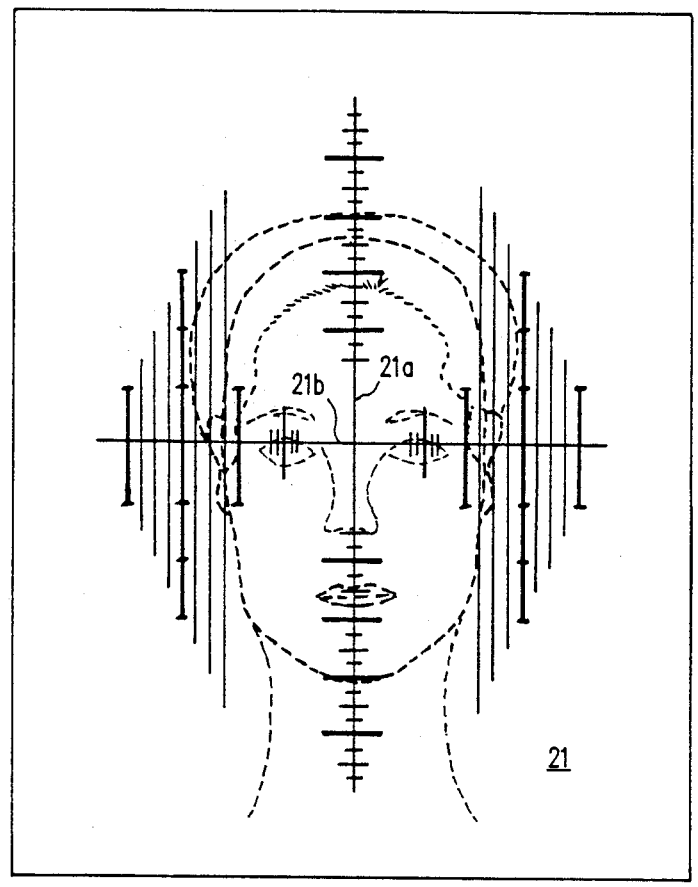
FIGS. 6 and 7 illustrate the grid members for evaluating the human head.
Figure 7:
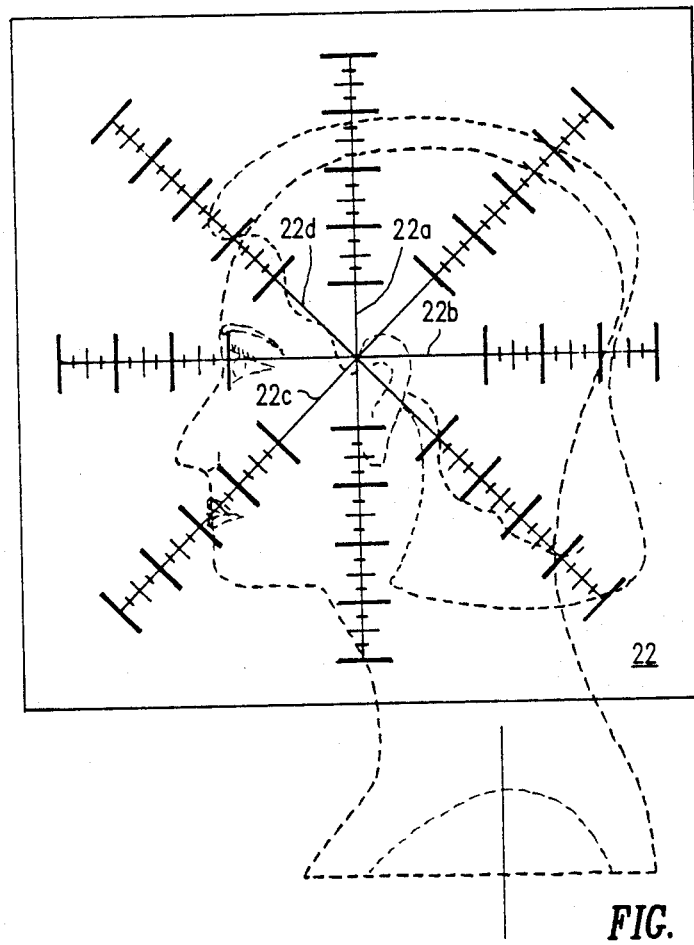

Another aspect of the present invention is illustrated in FIGS. 6 and 7. As shown in FIG. 6, a transparent member 21 contains grid lines which are useful in analyzing the bone structure and symmetry of the human head. Member 21 contains a vertical centerline 21a which is adapted to be aligned with a vertical line extending through the center of the bridge of the human nose. Centerline 21a contains a number of different, graduated horizontal lines as shown, for measuring distances to different portions of the human head from a reference horizontal line. Member 21 also contains a reference horizontal line 21b having a number of graduated vertical markings thereon for determining distances to different facial features from the vertical centerline of the head.

Member 21 is intended as a tool to analyze the bone structure of the individual, for example, to design a hairstyle. This is also an extension of one of DaVinci's concepts breaking the head into separate parts. For example, the front view of the head provided by member 21 provides information as to how high a hair style should be and where the fullness should be in the hair style. It also provides information as to where the ears are placed. A woman's earring size will depend a great deal on how long her ears are and also the contour of her face. Member 21 can also be used to design eyeglass frames, with the eyeglass frame following the structure of the face. Further, centerline 21 extending through the center of a nose provides a measure of the extent of crookedness in a nose, which can also be used as a guide in plastic surgery.

FIG. 7 illustrates a transparent member 22 having scaled graduations thereon which are useful in analyzing the human head from the side. Member 21 includes a vertical centerline 22a having graduated horizontal markings thereon. Member 22 also includes a graduated horizontal line 22b and two angled graduated lines 22c and 22d. The ideal head should be divided equally in front of the ear, as shown by centerline 22a in FIG. 7. Member 22 provides information as to whether the head is centered on the shoulders or whether is is forward on the shoulders. If it is forward, this indicates there needs to be volume in the back of a hair style to make the head appear as if it is more inclined back than it really is.

The above description set out a method practicing the present invention utilizing panel 11. However, it is possible to carry out the invention without such a panel and employing a computer to generate the desired data from the scanning data.

I claim:

1. Apparatus for measuring a plurality of attributes of a human body in relation to the values of said attributes in a theoretically ideal human body comprising:

a transparent proportional panel member having a plurality of sloping lines, said sloping lines being calibrated with the values of said attributes for said ideal human body for a range of heights of the human body:

a vertically oriented transparent measurement guide member having graduated height measurement indicia thereon:

means for moving said proportional panel member laterally behind said measurement guide with a person whose body is to be measured positioned behind said measurement guide:

means for determining the lateral position of said panel at which the uppermost of said sloping lines crosses a vertical centerline of said measurement guide at the top of the measured person's head: and means for marking on said measurement guide the vertical position thereon at which each of the other of said sloping lines crosses said centerline, whereby said markings on said measurement guide represent the locations of said attributes in an ideal body of the same height as the measured person.

2. Apparatus in accordance with claim 1 including means for measuring any difference between the values of said person being measured and the values of the corresponding attributes in said ideal body.

3. Apparatus in accordance with claim 1 in which said attributes represent the locations of different physical portions of the human body.

4. Apparatus in accordance with claim 3 in which the locations of said attributes on said ideal body are uniformly spaced from each other.

5. Apparatus in accordance with claim 4 in which eight such uniformly spaced attributes are employed.

6. Apparatus in accordance with claim 3 in which the locations of said attributes on said ideal body are not uniformly spaced from each other.

7. Apparatus in accordance with claim 1 in which said sloping lines on said proportional panel extend across the width of said panel, the ends of said sloping lines on both edges of said panel being uniformly spaced from each other.

8. Apparatus in accordance with claim 2 in which said measuring means includes a height scale on said measurement 9. Apparatus in accordance with claim 8 in which said marking means includes rod members affixed to said measurement guide.

* * * * *